(12) United States Patent
Parmee

(10) Patent No.: US 11,125,701 B2
(45) Date of Patent: Sep. 21, 2021

(54) TEST APPARATUS FOR X-RAY INSPECTION

(71) Applicant: Cheyney Design & Development Ltd., Royston (GB)

(72) Inventor: Richard Parmee, Litlington (GB)

(73) Assignee: Cheyney Design & Development LTD., Royston (GB)

( * ) Notice: Subject to any disclaimer, the term of this patent is extended or adjusted under 35 U.S.C. 154(b) by 0 days.

(21) Appl. No.: 16/619,541

(22) PCT Filed: May 29, 2018

(86) PCT No.: PCT/GB2018/051448
§ 371 (c)(1),
(2) Date: Dec. 5, 2019

(87) PCT Pub. No.: WO2018/215802
PCT Pub. Date: Nov. 29, 2018

(65) Prior Publication Data
US 2020/0232936 A1 Jul. 23, 2020

(30) Foreign Application Priority Data
May 26, 2017 (GB) .................................. 1708427

(51) Int. Cl.
*G01B 15/06* (2006.01)
*G01N 23/04* (2018.01)
(Continued)

(52) U.S. Cl.
CPC ....... *G01N 23/04* (2013.01); *G01N 35/00594* (2013.01); *G01N 33/02* (2013.01)

(58) Field of Classification Search
CPC .. G01N 23/04; G01N 35/00594; G01N 33/02; G01N 2223/643; G01N 2223/645; G01N 35/00623; G01N 35/00732
See application file for complete search history.

(56) References Cited

U.S. PATENT DOCUMENTS

2003/0105600 A1\* 6/2003 Alvi .................... G01N 33/2858
702/57
2007/0019841 A1\* 1/2007 Hirose .................... G01N 23/04
382/110
(Continued)

FOREIGN PATENT DOCUMENTS

EP 2163886 A1 3/2010
JP 2004245623 A 9/2004
(Continued)

OTHER PUBLICATIONS

International Search Report and Written Opinion for International Application No. PCT/GB/051448, dated Oct. 8, 2018, 10 pages.
(Continued)

*Primary Examiner* — Kiho Kim
(74) *Attorney, Agent, or Firm* — RatnerPrestia

(57) ABSTRACT

A test apparatus for challenging contaminant monitoring apparatus. The test apparatus includes contaminant provisions having a pre-selected property including any one or more of the group including composition, material, mass, size and/or shape of a contaminant. The test apparatus also includes identification provisions for identifying the presence of the contaminant provisions and/or for identifying the identity of the test apparatus. The contaminant provisions and the identification provisions are detectable and/or discriminateable by X-rays.

25 Claims, 2 Drawing Sheets

Figure 1:
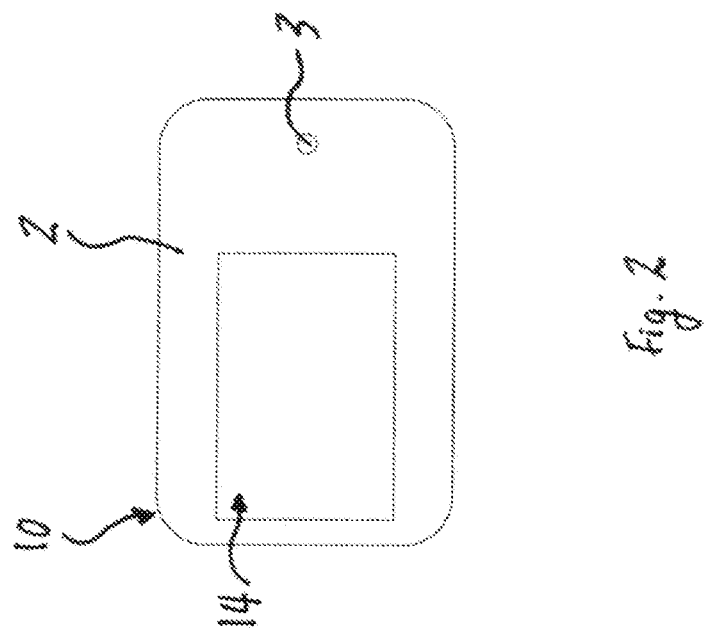

(51) Int. Cl.
*G01N 35/00* (2006.01)
*G01N 33/02* (2006.01)

(56) References Cited

U.S. PATENT DOCUMENTS

| | | | |
|---|---|---|---|
| 2008/0118026 A1* | 5/2008 | Ainsworth | G01N 33/02 378/20 |
| 2010/0135459 A1* | 6/2010 | Kabumoto | G01N 23/04 378/58 |
| 2010/0246930 A1* | 9/2010 | Dekker | G01N 33/02 382/141 |
| 2014/0322706 A1* | 10/2014 | Kayyem | G01N 35/00722 435/6.11 |

FOREIGN PATENT DOCUMENTS

| | | |
|---|---|---|
| JP | 2009031149 A | 2/2009 |
| WO | 2009112852 A1 | 9/2009 |

OTHER PUBLICATIONS

International Preliminary Report on Patentability for International Application No. PCT/GB2018/051448, dated Nov. 26, 2019, 8 pages.

* cited by examiner

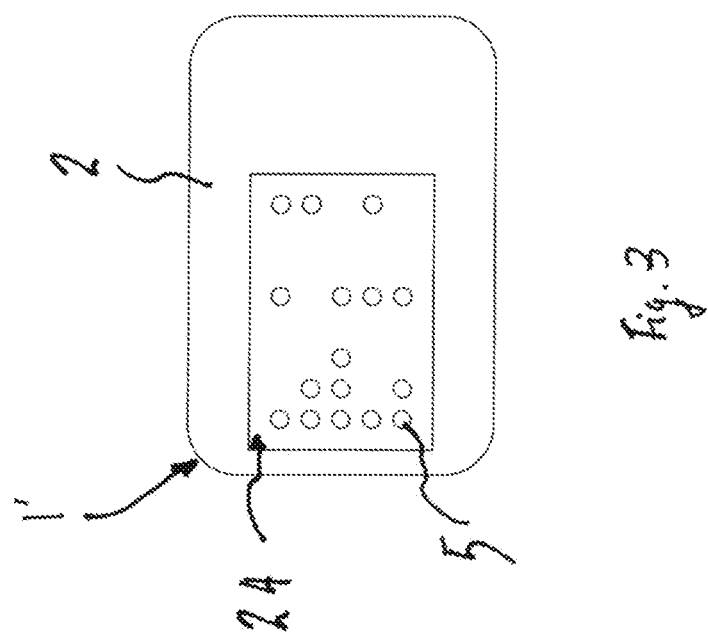

TEST APPARATUS FOR X-RAY INSPECTION

CROSS REFERENCE TO RELATED APPLICATIONS

This application is the U.S. National Stage filing of International Application No. PCT/GB2018/051448, filed on May 29, 2018, which claims priority to GB Application No. 1708427.8, filed on May 26, 2017, each of which being incorporated herein by reference for all purposes.

FIELD OF THE INVENTION

The present invention relates to test apparatus. In particular, the present invention relates to: a test apparatus for challenging contaminant monitoring apparatus; a contaminant monitoring apparatus, for scanning one or more items to be scanned; and a method for challenging contaminant monitoring apparatus.

BACKGROUND OF THE INVENTION

It is important to ensure that food products leaving a production line are not contaminated by foreign items which should not be found in the foodstuff by a consumer. As such, contaminant monitoring systems are used to scan products on production lines before the food products leave the site of manufacture/processing. The monitoring systems may include metal detectors or, more often, X-ray scanning apparatus, which is capable of detecting objects having only a slightly different radiological density or consistency than the desired foodstuff. In particular, X-ray scanners are used to detect metal, glass, mineral stones, some plastics and/or bones in meat foodstuffs. One can test operation of the monitoring system by running through the production line one or more test samples having pre-selected properties of composition, material, mass, size and/or shape of a contaminant. Such test samples are used to ensure that the apparatus has been properly set up and are introduced, at either regular or random intervals, to challenge the apparatus and ensure compliance with stringent monitoring requirements set by a customer. For instance, customers of food manufacturers will insist on monitoring and auditing the logs created by such monitoring systems so as to ensure that they have been properly tested throughout operation.

Test samples are known in the art and typically have a contaminant of a pre-selected property and a bar code for identification of the test sample. Such test samples and existing monitoring systems rely on line-of-sight for reading the barcode, which is now considered a disadvantage in a fast moving production line. For instance, the barcode may be easily masked by food products on the production line or itself if upside down.

Further, although test samples are often detected by the monitoring system, if it is not working correctly, even if implementing challenges, one will not know whether various food products containing contaminants have passed through undetected. As such, it is also conceivable that, sometimes, the test sample may pass through the apparatus unnoticed.

SUMMARY OF THE INVENTION

Accordingly, the present invention is aimed at providing a test apparatus without the disadvantages associated with the prior art test samples. The present invention is also aimed at providing an improved contaminant monitoring apparatus and associated method.

The present invention is also aimed at identifying any malpractice in which a user accidentally or deliberately puts an incorrect test sample through the monitoring apparatus.

According to a first aspect of the present invention, there is provided a test apparatus, for challenging contaminant monitoring apparatus, the test apparatus comprising:
  contaminant means, having a pre-selected property comprising any one or more of the group comprising composition, material, mass, size and/or shape of a contaminant; and
  identification means, for identifying the presence of the contaminant means and/or for identifying the identity of the test apparatus;
wherein the contaminant means and the identification means are detectable and/or discriminateable by X-rays.

Preferably, the pre-selected property relates to an actual contaminant or a simulated contaminant.

Preferably, both the contaminant means and identification means are capable of being scanned by a single X-ray source, or both scanned by a plurality of X-ray sources.

Preferably, the identification means is an X-ray-readable identification means.

Preferably, the identification means is readable by X-rays so as to identify one or more pre-selected properties of the contaminant means.

Preferably, the contaminant means and the identification means are a single contaminant/identification means.

Preferably, the contaminant means and identification means are separate and distinct contaminant means and identification means.

Preferably, the identification means comprises a metallic plate, or plate of material substantially opaque to X-rays. Most preferably, the metallic plate is stainless steel. Alternatively, and most preferably, the plate of material substantially opaque to X-rays comprises:
  a plastics material comprising a dopant which makes it substantially opaque to X-rays; or
  a coated or laminated plastics material in which a coating or layer comprises a material substantially opaque to X-rays.

Preferably, the plastics material, coating and/or layer comprises a metallic salt or metal particulate, which is preferably barium sulphate.

Most preferably, the plate is of sufficient dimensions so as to not go unnoticed by said contaminant monitoring apparatus.

Preferably, the identification means comprises one or more apertures and/or recesses, or other indicia, which are capable of being detected through X-ray scanning. Most preferably, each aperture or recess is ≥2 mm in diameter (or longest dimension). Those skilled in the art will understand the term 'aperture' to mean a hole, which is made in the plate after manufacture or formed in the plate during manufacturing. In addition, the term 'recess' will be understood to mean a reduction in thickness of the plate, again which is made in the plate after manufacture or formed in the plate during manufacturing. In each case, such an aperture, recess or other indicia, provides a discernible difference to the plate generally when scanned using X-rays.

Preferably, the apertures or recesses provide an array, which is capable of conveying data to said contaminant monitoring apparatus, the array comprises:
  means for identifying the presence of the contaminant means;

means for identifying the identity of the test apparatus; and/or means for identifying one or more pre-selected properties of the contaminant means.

Preferably, the contaminant means and the identification means are spatially located, so as to be individually identifiable when being scanned.

Preferably, the contaminant means and identification means are located in distinct regions of the test apparatus.

Preferably, the identification means is significantly larger than the contaminant means, so as to ensure that the test apparatus does not go unnoticed.

Preferably, the test apparatus further comprises a housing, for receipt of the contaminant means and the identification means, wherein the housing is manufactured from a material having a relatively low absorption of X-rays.

Preferably, the contaminant monitoring apparatus comprises X-ray contaminant monitoring apparatus.

Figure 2:
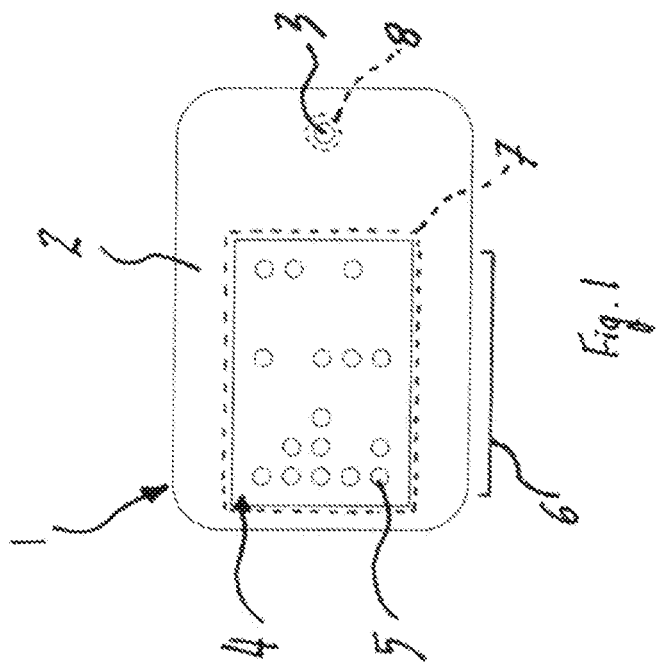

A test apparatus, for challenging contaminant monitoring apparatus, substantially as herein disclosed, with reference to FIG. 1 or 2 of the accompanying drawings and/or any example described herein.

According to a second aspect, the present invention provides a contaminant monitoring apparatus, for scanning one or more items to be scanned, comprising:
 a test apparatus comprising a contaminant means and an identification means; and
 X-ray scanning means, for scanning the test apparatus; wherein the X-ray scanning means is configured to detect and/or discriminate between the contaminant means and the identification means.

Preferably, the contaminant monitoring apparatus comprises X-ray contaminant monitoring apparatus.

Preferably, the contaminant means and identification means of the test apparatus are both responsive to X-rays.

Preferably, the scanning means is capable of:
 identifying the presence of the contaminant means;
 identifying the identity of the test apparatus; and/or
 identifying one or more pre-selected properties of the contaminant comprising any one or more of the group comprising composition, material, mass, size and/or shape of the contaminant.

Preferably, the X-ray scanning means comprises:
 means for identifying the presence of the contaminant means;
 means for identifying the identity of the test apparatus; and/or
 means for identifying one or more pre-selected properties of the contaminant comprising any one or more of the group comprising composition, material, mass, size and/or shape of the contaminant.

Preferably comprising a single X-ray detector for scanning both the contaminant means and identification means, or a plurality of X-ray detectors which each scan both the contaminant means and identification means. Most preferably, the X-ray scanner(s) is/are the same as the scanner which scans a food product to be tested.

Preferably, the X-ray scanning means is capable of reading the identification means of the test apparatus.

Preferably, the X-ray scanning means is capable of reading an array of apertures and/or recesses, or other indicia forming the identification means of the test apparatus.

Preferably, in use, data relating to the one or more pre-selected properties of the contaminant means is directly sourced from the array provided by the test apparatus, or from a combination of the detected array and a database of such properties associated with known arrays.

Preferably comprising means for diverting the test apparatus, or the test apparatus and one or more surrounding items.

Preferably comprising a test apparatus according to any one or more features of the first aspect.

According to a further aspect, the present invention provides a method for challenging contaminant monitoring apparatus, the method comprising:
 submitting a test apparatus comprising contaminant means and identification means to the contaminant monitoring apparatus;
 X-ray scanning the test apparatus so as to detect and/or discriminate between the contaminant means and the identification means.

Preferably comprising X-ray scanning so as to:
 identify the presence of the contaminant means;
 identify the identity of the test apparatus; and/or
 identify one or more pre-selected properties of the contaminant comprising any one or more of the group comprising composition, material, mass, size and/or shape of the contaminant.

Preferably comprising X-ray reading the identification means.

Preferably comprising X-ray reading an array of apertures and/or recesses, or other indicia forming the identification means of the test apparatus.

Preferably comprising scanning and detecting a property of the contaminant means comprising any one or more of the group comprising composition, material, mass, size and/or shape of the contaminant.

Preferably comprising comparing a detected property of the contaminant means with a predicted property of the contaminant means.

Preferably comprising adhering to a schedule for submitting a specific test apparatus to the contaminant monitoring apparatus and comparing a/the detected property with a/the predicted property.

Preferably, analysing a scan of the test apparatus so as to identify a region encapsulating the identification means and creating a masked region to remove such region from further analysis.

Preferably, analysing a scan of the test apparatus so as to identify a region encapsulating the contaminant means and further analysing the contents of such region to determine a property of the contaminant.

Preferably comprising a test apparatus according any one or more features of the first aspect.

Preferably, diverting the test apparatus, or diverting the test apparatus and one or more surrounding items.

A method for challenging contaminant monitoring apparatus, substantially as herein disclosed, with reference to the accompanying description and/or any example described herein.

Advantageously, test apparatus of the present invention are easily detected through X-ray scanning and, therefore, cannot readily pass through the contaminant monitoring apparatus unnoticed. In particular, by using a plate of metal or material substantially opaque to X-rays, and removing parts thereof or thinning such parts (through apertures or recesses), the likelihood of the test apparatus passing through contaminant monitoring equipment unnoticed is substantially eliminated.

Advantageously, as the X-ray scanner of the apparatus is used to detect both the contaminant means and the identification means, a separate scanner for detecting the identification means is not required.

Advantageously, X-ray scanning of the identification means does not rely upon line-of-sight reading of the identification means.

Further, owing to the arrangement of the identification means, including a plurality of apertures, recesses or other indicia which are readable by the X-ray scanner, it is easier to identify the test apparatus, as the test apparatus is detectable through food products, even if a number are placed on top of it.

The contaminant monitoring apparatus may be programmed with a testing schedule, which will identify when to submit a specific test apparatus as a challenge, and which test apparatus to use. A log is kept so as to confirm that the correct test apparatus has been passed through the system. The apparatus can easily verify that the correct test apparatus has been submitted, and not some unexpected contaminant.

Test apparatus of the present invention are ideal as they are easily added to a production line whilst in motion. If they are obscured or upside down, they are still readable. Those skilled in the art will understand that there is a considerable cost implication in stopping a production line and such occurrences are highly undesired.

Advantageously, by making the contaminant means a single test piece or particle, an improved test apparatus is provided which helps to ensure that a contaminant monitoring apparatus accurately detects the test piece or particle itself, and not only one test piece or particle of a plurality of such test pieces or particles.

The present invention relates to a test apparatus, which should be understood to include such things as test cards, test sticks, test pucks, or the like.

For the avoidance of doubt, owing to the nature of the scanning undertaken, only those contaminants which are detectable by X-rays can be detected in the food products and/or the test apparatus. Typically, such contaminants are radiographically opaque foreign bodies, i.e. parts which appear denser than the expected density of the food product being tested.

BRIEF DESCRIPTION OF THE DRAWING FIGURES

The invention will now be disclosed, by way of example only, with reference to the following drawings, in which:
FIG. 1 is a plan view of a test apparatus;
FIG. 2 is a plan view of a further test apparatus; and
FIG. 3 is a plan view of a yet further test apparatus.

DETAILED DESCRIPTION OF THE INVENTION

A test apparatus, generally identified by reference 1, is shown in FIG. 1, which test apparatus 1 includes a housing 2, and a contaminant 3 and an identification 4 located within the housing 2. In this embodiment, the contaminant 3 and identification 4 are fully encapsulated by the housing 2, but it is not necessary for them to be fully-encapsulated. The test apparatus 1 is a type of apparatus which is used to challenge X-ray contaminant monitoring apparatus, so as to verify correct operation of the primary function of the contaminant monitoring apparatus to detect contaminants in food products on a production line.

The housing 2 securely holds the contaminant 3 and identification 4 in a spaced relationship, such that the contaminant 3 and identification 4 are separate and individually detectable and/or discriminateable by X-rays. The housing 2 is manufactured from acrylic, although it could be manufactured from another material which has a relatively low absorption of X-rays, for example polyethylene.

The contaminant 3 may be an actual contaminant or a simulated contaminant, for example a piece of metal, bone or glass of specific size and weight, or of other pre-selected properties. More generally, contaminant 3 has one or more pre-selected properties relating to, for example, the composition, material, mass, size and/or shape of the contaminant.

The identification 4, which is a metal plate (although it could be a plate of material substantially opaque to X-rays), includes a plurality of circular apertures 5 through the plate which are arranged in an array 6, which array 6 and apertures 5 can be read by an X-ray scanner so as to identify the test apparatus 1 per se, and identify one or more pre-selected properties of the contaminant 3. The metal plate is manufactured from stainless steel, and each aperture 5 is approx. 2 mm in diameter.

Alternatively, a test apparatus, identified generally by reference 10, is shown in FIG. 2. The test apparatus 10 has various similarities with the test apparatus 1 of FIG. 1, and only the differences will be discussed in detail. In particular, the main difference is an identification 14 of test apparatus 10, which is a metal plate (although it could be a plate of material substantially opaque to X-rays) having no array, apertures or recesses therein. Properties of the contaminant 3 are determinable by X-ray scanning the contaminant 3, however, only limited information can be conveyed by the identification 14 of test apparatus 10. As such, test apparatus 10 provides a simplified test apparatus 10 for use with contaminant monitoring apparatus where one simply wishes to test and identify the presence or existence of a contaminant, rather than be able to verify or cross-reference one or more pre-selected properties of the contaminant.

The identification 4; 14 is of sufficient dimensions so as to not go unnoticed by contaminant monitoring apparatus. By way of example, the identification 4; 14 could have minimum dimensions of approx. 10 mm by 10 mm as viewed by the X-ray scanner, and could extend up to, say, 50 mm by 50 mm. Beyond this limit practicality reduces, although there are no real maximum dimensions. Test apparatus 1; 10 is intended to be placed on a production line and passed through contaminant monitoring apparatus, which are provided to scan and detect contaminants in food products passing along the production line. Test apparatus 1; 10 may be placed on a moving production line, preventing the need to slow down or stop the production line.

A contaminant monitoring apparatus (not shown) includes an X-ray scanner for identifying and locating any contaminants in the food product being scanned. Such apparatus are known in the art. Where the present invention differs is that there is no need for additional line-of-sight scanners for detecting the identity of the test apparatus 1; 10. X-ray scanning is used to detect and/or discriminate between the contaminant 3 and the identification 4, as they are both responsive to X-rays. Accordingly, the contaminant monitoring apparatus includes additional hardware for processing and analysing the X-ray images of the contaminant 3 and identification 4. The contaminant monitoring equipment is programmed to provide a schedule of challenges, which involves submitting a specific test apparatus 1; 10 to the contaminant monitoring apparatus at the required time or interval indicated in the schedule. Such a schedule is provided so as to be able to log and audit the challenges introduced to the contaminant monitoring apparatus and verify that its contaminant detecting function is working correctly. By way of an alternative, the contaminant monitoring apparatus may include a plurality of X-ray scanners—in particular, the apparatus could use DEXA (dual-energy X-ray absorptiometry), involving the use of scanning at two different energy levels.

The contaminant monitoring apparatus includes a diverter—or the apparatus is arranged to implement diversion—such that any food product in which there is believed to be a contaminant or detected test apparatus 1; 10, or even any food product surrounding the detected test apparatus 1; 10 or contaminant-containing food product, can be diverted from the main production line. Once diverted, the test apparatus is retrieved for further use and the food products are either disposed of or further tested.

In use, the test apparatus 1:10 is submitted to the contaminant monitoring apparatus so as to check it is working effectively. Test apparatus 1; 10 is passed through the X-ray scanner of the monitoring apparatus either at the same time or independently of one or more food products. The X-ray scanner of the apparatus detects and/or discriminates between the contaminant 3 and the identification 4.

With respect to test apparatus 10, the apparatus detects the presence or existence of the identification 4 and one or more properties of the contaminant 3. Accordingly, one can easily verify that the test apparatus 10 has been passed through the contaminant monitoring apparatus, but one cannot verify that the detected contaminant is expected from such a test apparatus 10.

With respect to test apparatus 1, the X-ray scanner reads the array 6 of apertures 5, forming the identification 4, and detects one or more properties of the contaminant 3. In so doing, the apparatus determines one or more predicted properties of the contaminant 3 from the identification 4 and the apparatus determines one or more detected properties of the contaminant 3 through X-ray scanning the contaminant per se. The predicted one or more properties and the detected one or more properties are then compared so as to verify that the predicted and determined properties are substantially the same. This particular feature prevents misuse of the contaminant monitoring apparatus, such that an operator cannot, by mistake or deliberately, introduce anything other than the expected test apparatus without such misuse being detected. Data relating to one or more pre-selected properties of the contaminant 3 is either directly sourced from the array 6 or from a combination of information from the detected array 6 and a database of such pre-selected properties associated with known detectable arrays. Certification data specific to the contaminant may be incorporated in the array 6 or retrieved from a database using the array 6. More generally, certification data may be incorporated in the identification means or may be retrieved from a database using the identification means. Such certification data may provide a unique reference for the purpose of validation, being either a serial number or certification number.

In a further embodiment, once scanned, a resulting X-ray scan of the test apparatus 1; 10 is analysed so as to identify a region—shown in FIG. 1 by a stippled line having a reference 7—encapsulating the identification 4 and create a masked region 7 to remove such region 7 from further analysis. In particular, the masked region 7 prevents the identification 4—which is also a contaminant in this exemplary embodiment—from being analysed further, and thus prevents a false auditing trail. The resulting X-ray scan is also analysed so as to identify a further region—shown in FIG. 1 by a stippled line having a reference 8—encapsulating the contaminant 3, which region 8 is then further analysed so as to determine one or more detected properties of the contaminant 3.

Although the test apparatus has been described above as including a housing, and contaminant and identification located within the housing, in a simplified version the test apparatus could be configured such that the identification also provides the housing. For practical reasons, the contaminant would be capable of being differentiated from the identification, as per the claimed invention, and this would involve a form of separation which would make them detectable and/or discriminateable by X-rays. Accordingly, the present invention also provides a test apparatus consisting of an identification means and a contaminant means.

FIG. 3 shows a further alternative test apparatus, identified generally by reference 1'. The test apparatus 1' has various similarities with the test apparatus 1 of FIG. 1, and only the differences will be discussed in detail. In particular, the main difference is the absence of a separate contaminant 3. In this example, a contaminant and an identification is provided by a single contaminant/identification 24. The contaminant/identification 24 is a metal plate (although it could be a plate of material substantially opaque to X-rays) and it includes a plurality of circular apertures 5 which are arranged in an array. Such apertures 5 can be read by an X-ray scanner so as to identify the test apparatus 1' per se, and/or identify one or more pre-selected properties of the contaminant 24. The metal plate is manufactured from stainless steel, and each aperture 5 is approx. 2 mm in diameter. Test apparatus 1' may be used in a contaminant monitoring apparatus in a similar way to the test apparatus 1:10; however, detection of properties of the contaminant per se is more limited.

Preferably, so that an operator of contaminant monitoring apparatus can identify which test apparatus to put through the monitoring apparatus, the test apparatus may include an operator-readable identification or other indicia, which is in addition to the identification means which is detectable and/or discriminateable by X-rays. Most preferably, the operator-readable identification is a code, or potentially a serial number, which may also include a manufacturer's name and/or one or more details of the contaminant. For example, such a code might read: Size of contaminant "5.0 mm", Material of contaminant "SS316" (Stainless steel grade 316), and Certification number "7737", together with manufacturer and manufacturer's part number.

The invention claimed is:
1. A test sample that is configured to be monitored by a contaminant monitoring apparatus for identifying a contaminant on the test sample, the test sample comprising:
   a contaminant having a pre-selected property comprising any one or more of the group comprising composition, material, mass, size and/or shape of a contaminant; and
   an X-ray readable identifier for identifying an identity of the test sample;
   wherein the contaminant and the identifier are detectable and/or discriminateable by X-rays, and
   wherein the identifier comprises apertures and/or recesses, which (i) provide an array that is configured to convey data for identifying identities of the test sample and the contaminant to said contaminant monitoring apparatus, and (ii) are capable of being detected through X-ray scanning, and
   wherein an arrangement of the array corresponds to the pre-selected property of the contaminant.
2. The test sample as claimed in claim 1, wherein the contaminant and identifier are separate and distinct contaminant and identifier.

3. The test sample as claimed in claim 1, wherein the identifier comprises a metallic plate, or a plate of material substantially opaque to X-rays.

4. The test sample as claimed in claim 3, wherein the plate of material substantially opaque to X-rays comprises:
   a plastics material comprising a dopant which makes the plate substantially opaque to X-rays; or
   a coated or laminated plastics material in which a coating or layer comprises a material substantially opaque to X-rays.

5. The test sample as claimed in claim 1, wherein the test sample further comprises a housing for receipt of the contaminant and the identifier, wherein the housing comprises a material having a relatively low absorption of X-rays.

6. A contaminant monitoring apparatus for scanning one or more items to be scanned, said contaminant monitoring apparatus comprising:
   the test sample as claimed in claim 1 comprising the contaminant and the identifier; and X-ray scanning apparatus for scanning the test sample;
   wherein the X-ray scanning apparatus is configured to detect and/or discriminate between the contaminant and the identifier.

7. The apparatus as claimed in claim 6, wherein the X-ray scanning apparatus comprises:
   an X-ray detector for identifying a presence of the contaminant;
   an X-ray detector for identifying an identity of the test sample; and/or
   an X-ray detector for identifying one or more pre-selected properties of the contaminant comprising any one or more of the group comprising composition, material, mass, size and/or shape of the contaminant.

8. The apparatus as claimed in claim 6 comprising a single X-ray detector for scanning both the contaminant and the identifier, or a plurality of X-ray detectors which each scan both the contaminant and the identifier.

9. The apparatus as claimed in claim 6, wherein the X-ray scanning apparatus is configured to read the identifier of the test sample.

10. The apparatus as claimed in claim 9, wherein the X-ray scanning apparatus is configured to read the array of apertures and/or recesses, or other indicia forming the identifier of the test sample.

11. The apparatus as claimed in claim 10, wherein, in use, data relating to one or more pre-selected properties of the contaminant is directly sourced from the array provided by the test sample, or from a combination of the detected array and a database of such properties associated with known arrays.

12. The test sample of claim 1, wherein the pre-selected property is configured for determining a detected property of the contaminant, wherein the array is capable of conveying data for determining a predicted property of the contaminant, and the X-ray readable identifier is further configured for identifying the predicted property of the contaminant based upon the array, and wherein an arrangement of the array corresponds to the predicted property of the contaminant allowing said contaminant monitoring apparatus to compare and verify the predicted property of contaminant with the detected property of contaminant.

13. The test sample of claim 1, wherein the X-ray readable identifier is configured for identifying certification data, a serial number or a certification number specific to the pre-selected property of the contaminant, and the array is configured to convey data for identifying the identity of the test sample and the certification data, the serial number or the certification number specific to the pre-selected property of the contaminant to said contaminant monitoring apparatus.

14. The test sample of claim 1, wherein the identifier comprises a metallic plate or plate of material that is opaque to X-rays, and the plate comprises said apertures and/or recesses which, when detected through X-ray scanning, provide a discernable difference between the apertures and/or recesses and the plate such that the plate and the apertures and/or recesses provide said array that is capable of conveying data for identifying the identities of the test sample and the pre-selected property of the contaminant to said contaminant monitoring apparatus.

15. The test sample of claim 1, wherein the contaminant and the identifier are detectable and/or discriminateable by X-rays but are separate and distinct thereby enabling identification of a first separate and distinct region of the test sample which encapsulates the contaminant and a second separate and distinct region of the test sample which encapsulates the identifier but not the contaminant.

16. The test sample of claim 1, wherein the array is capable of conveying data for identifying the identities of the test sample as well as the pre-selected property of the contaminant to said contaminant monitoring apparatus.

17. In a test sample that is configured to be monitored by a contaminant monitoring apparatus for identifying a contaminant on the test sample, the test sample comprising: a contaminant having a pre-selected property comprising any one or more of the group comprising composition, material, mass, size and/or shape of a contaminant; and an X-ray readable identifier for identifying an identity of the test sample, wherein the contaminant and the identifier are detectable and/or discriminateable by X-rays, and wherein identifier comprises apertures and/or recesses, which (i) provide an array configured to convey data for identifying the identities of the test sample and the contaminant to said contaminant monitoring apparatus, and (ii) are capable of being detected through X-ray scanning, and wherein an arrangement of the array corresponds to the pre-selected property of the contaminant, the method comprising:
   submitting the test sample comprising the contaminant and the identifier to the contaminant monitoring apparatus; and
   X-ray scanning the test sample so as to detect and/or discriminate between the contaminant and the identifier.

18. The method as claimed in claim 17 comprising X-ray scanning so as to:
   identify a presence of the contaminant;
   identify an identity of the test sample; and/or
   identify one or more pre-selected properties of a contaminant comprising any one or more of the group comprising composition, material, mass, size and/or shape of a contaminant.

19. The method as claimed in claim 17 comprising X-ray reading the identifier.

20. The method as claimed in claim 19 comprising X-ray reading the array of apertures and/or recesses, or other indicia forming the identifier of the test sample.

21. The method as claimed in claim 17 comprising scanning and determining a property of the contaminant comprising any one or more of the group comprising composition, material, mass, size and/or shape of a contaminant.

22. The method as claimed in claim 21 comprising comparing a detected property of the contaminant with a predicted property of the contaminant.

23. The method as claimed in claim 22 comprising adhering to a schedule for submitting a specific test sample to the contaminant monitoring apparatus and comparing the detected property with the predicted property.

24. The method as claimed in claim 17 comprising analyzing a scan of the test sample so as to:
   (i) identify a region encapsulating the identifier and creating a masked region to remove said region from further analysis, and
   (ii) identify a region encapsulating the contaminant and further analyzing the contents of such region to determine a property of a contaminant.

25. The method as claimed in claim 17 wherein the contaminant has a pre-selected property comprising any one or more of the group comprising composition, material, mass, size and/or shape of the contaminant; and the identifier, for identifying a presence of the contaminant and/or for identifying an identity of the test sample; wherein the contaminant and the identifier are detectable and/or discriminateable by X-rays.

* * * * *